(12) United States Patent
Woloszko et al.

(10) Patent No.: US 8,114,071 B2
(45) Date of Patent: Feb. 14, 2012

(54) HARD TISSUE ABLATION SYSTEM

(75) Inventors: Jean Woloszko, Austin, TX (US);
Kenneth R. Stalder, Redwood City, CA (US)

(73) Assignee: ArthroCare Corporation, Austin, TX (US)

( * ) Notice: Subject to any disclaimer, the term of this patent is extended or adjusted under 35 U.S.C. 154(b) by 1295 days.

(21) Appl. No.: 11/754,551

(22) Filed: May 29, 2007

(65) Prior Publication Data

US 2007/0282323 A1 Dec. 6, 2007

Related U.S. Application Data

(60) Provisional application No. 60/809,581, filed on May 30, 2006.

(51) Int. Cl.
*A61B 18/14* (2006.01)

(52) U.S. Cl. .............................. 606/32; 606/41

(58) Field of Classification Search .............. 606/32, 606/41
See application file for complete search history.

(56) References Cited

U.S. PATENT DOCUMENTS

| | | | |
|---|---|---|---|
| 2,050,904 A | 4/1936 | Trice | 219/31 |
| 2,056,377 A | 10/1939 | Wappler | 125/303 |
| 3,633,425 A | 1/1972 | Sanford | 73/356 |
| 3,707,149 A | 12/1972 | Hao et al. | 128/303.14 |
| 3,718,617 A | 2/1973 | Royal | 260/30.4 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,963,030 A | 6/1976 | Newton | 606/40 |
| 3,964,487 A | 6/1976 | Judson | 606/39 |
| 3,970,088 A | 7/1976 | Morrison | 128/303 |
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| D249,549 S | 9/1978 | Pike | D24/144 |
| 4,114,623 A | 9/1978 | Meinke et al. | 606/39 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |

(Continued)

FOREIGN PATENT DOCUMENTS

DE 3119735 1/1983

(Continued)

OTHER PUBLICATIONS

European Examination Report 2 for EP 04708664 5pgs, May 3, 2010.

(Continued)

*Primary Examiner* — Lee Cohen
(74) *Attorney, Agent, or Firm* — Matthew Scheele; Brian Szymczak

(57) ABSTRACT

An electrosurgical system and method for treating hard and soft tissues in the body comprises a shaft, a distal end section, an active electrode associated with the distal end section, a first fluid supply adapted to deliver a first electrically conductive fluid to the target site, and a second fluid supply adapted to deliver a second electrically conductive fluid to the active electrode. The system is adapted to treat a wide variety of hard tissues such as, for example, bones, calcified structures, calcified deposits, teeth, plaque, kidney-stones, gall-stones and other types of tissue by generating plasma in the vicinity of the active electrode, and applying the plasma to the tissue or structures.

23 Claims, 11 Drawing Sheets

U.S. PATENT DOCUMENTS

| | | | |
|---|---|---|---|
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,240,441 A | 12/1980 | Khalil | 600/505 |
| 4,248,231 A | 2/1981 | Herczog et al. | 128/303 |
| 4,301,801 A | 11/1981 | Schneiderman | 606/38 |
| 4,326,529 A | 4/1982 | Doss et al. | 128/303 |
| 4,346,715 A | 8/1982 | Gammell | 607/99 |
| 4,363,324 A | 12/1982 | Kusserow | 607/64 |
| 4,378,801 A | 4/1983 | Oosten | 606/37 |
| 4,381,007 A | 4/1983 | Doss | 128/303 |
| 4,418,692 A | 12/1983 | Guay | 606/42 |
| 4,474,179 A | 10/1984 | Koch | 606/40 |
| 4,476,862 A | 10/1984 | Pao | 128/303 |
| 4,509,532 A | 4/1985 | DeVries | 128/736 |
| 4,520,818 A | 6/1985 | Mickiewicz | 606/40 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,572,206 A | 2/1986 | Geddes et al. | 600/505 |
| 4,580,557 A | 4/1986 | Hertzmann | 606/12 |
| 4,587,975 A | 5/1986 | Salo et al. | 600/506 |
| 4,590,934 A | 5/1986 | Malis et al. | 128/303 |
| 4,593,691 A | 6/1986 | Lindstrom et al. | 128/303 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 606/41 |
| 4,727,874 A | 3/1988 | Bowers et al. | 128/303 |
| 4,750,902 A | 6/1988 | Wuchinich et al. | 604/22 |
| 4,765,331 A | 8/1988 | Petruzzi et al. | 128/303 |
| 4,785,823 A | 11/1988 | Eggers et al. | 128/692 |
| 4,805,616 A | 2/1989 | Pao | 128/303 |
| 4,823,791 A | 4/1989 | D'Amelio et al. | 123/303 |
| 4,832,048 A | 5/1989 | Cohen | 128/786 |
| 4,860,752 A | 8/1989 | Turner | 607/102 |
| 4,898,169 A | 2/1990 | Norman et al. | 606/42 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,943,290 A | 7/1990 | Rexroth et al. | 606/45 |
| 4,955,377 A | 9/1990 | Lennox et al. | 607/105 |
| 4,966,597 A | 10/1990 | Cosman | 606/50 |
| 4,967,765 A | 11/1990 | Turner et al. | 128/785 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,026,387 A | 6/1991 | Thomas | 606/169 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,057,106 A | 10/1991 | Kasevich et al. | 606/33 |
| 5,057,743 A | 10/1991 | Krasko et al. | 313/639 |
| 5,078,717 A | 1/1992 | Parins et al. | 606/48 |
| 5,080,660 A | 1/1992 | Buelna | 606/45 |
| 5,083,565 A | 1/1992 | Parins et al. | 600/374 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,092,339 A | 3/1992 | Geddes et al. | 606/505 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,174,304 A | 12/1992 | Latina et al. | 607/141 |
| 5,178,620 A | 1/1993 | Eggers et al. | 606/41 |
| 5,183,338 A | 2/1993 | Wickersheim et al. | 374/131 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,207,675 A | 5/1993 | Canady | 606/40 |
| 5,217,457 A | 6/1993 | Delahuerga et al. | 606/42 |
| 5,217,459 A | 6/1993 | Kamerling | 606/48 |
| 5,249,585 A | 10/1993 | Turner et al. | 607/99 |
| 5,255,980 A | 10/1993 | Thomas et al. | 374/161 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,281,218 A | 1/1994 | Imran | 606/41 |
| 5,282,799 A | 2/1994 | Rydell | 606/48 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,318,563 A | 6/1994 | Malis et al. | 606/38 |
| 5,324,254 A | 6/1994 | Phillips | 604/21 |
| 5,330,470 A | 7/1994 | Hagen | 606/42 |
| 5,334,140 A | 8/1994 | Phillips | 604/35 |
| 5,334,183 A | 8/1994 | Wuchinich | 606/46 |
| 5,334,193 A | 8/1994 | Nardella | 606/41 |
| 5,336,220 A | 8/1994 | Ryan et al. | 604/22 |
| 5,342,357 A | 8/1994 | Nardella | 606/40 |
| 5,366,443 A | 8/1994 | Eggers et al. | 252/511 |
| 5,348,554 A | 9/1994 | Imran et al. | 606/41 |
| 5,363,324 A | 11/1994 | Hashimoto et al. | 365/156 |
| 5,370,675 A | 12/1994 | Edwards et al. | 607/101 |
| 5,374,261 A | 12/1994 | Yoon | 604/385.01 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,882 A | 6/1995 | Jackman et al. | 607/122 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |
| 5,449,356 A | 9/1995 | Walbrink et al. | 606/49 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,458,597 A | 10/1995 | Edwards et al. | 606/41 |
| 5,472,443 A | 12/1995 | Cordis et al. | 606/48 |
| 5,486,161 A | 1/1996 | Lax et al. | 604/22 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,505,730 A | 4/1996 | Edwards et al. | 606/41 |
| 5,514,130 A | 5/1996 | Baker | 606/41 |
| 5,540,683 A | 7/1996 | Ichikawa et al. | 606/40 |
| 5,542,915 A | 8/1996 | Edwards et al. | 604/22 |
| 5,549,598 A | 8/1996 | O'Donnell, Jr. | 606/6 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,573,533 A | 11/1996 | Strul | 606/34 |
| 5,584,872 A | 12/1996 | LaFontaine et al. | 607/117 |

| | | | |
|---|---|---|---|
| 5,588,960 A | 12/1996 | Edwards et al. ............... 604/20 |
| 5,599,350 A | 2/1997 | Schulze et al. ............... 606/51 |
| 5,609,151 A | 3/1997 | Mulier et al. ............... 128/642 |
| 5,633,578 A | 5/1997 | Eggers et al. ............... 323/301 |
| 5,634,921 A | 6/1997 | Hood et al. ............... 606/5 |
| 5,643,304 A | 7/1997 | Schechter et al. ............ 606/171 |
| 5,647,869 A | 7/1997 | Goble et al. ............... 606/37 |
| 5,658,278 A | 8/1997 | Imran et al. ............... 606/41 |
| 5,660,567 A | 8/1997 | Nierlich et al. ......... 439/620.21 |
| 5,662,680 A | 9/1997 | Desai ............... 606/210 |
| 5,676,693 A | 10/1997 | LaFontaine et al. ............ 607/116 |
| 5,681,282 A | 10/1997 | Eggers et al. ............... 604/114 |
| 5,683,366 A | 11/1997 | Eggers et al. ............... 604/114 |
| 5,697,281 A | 12/1997 | Eggers et al. ............... 604/114 |
| 5,697,536 A | 12/1997 | Eggers et al. ............... 604/114 |
| 5,697,882 A | 12/1997 | Eggers et al. ............... 604/114 |
| 5,697,909 A | 12/1997 | Eggers et al. ............... 604/114 |
| 5,697,927 A | 12/1997 | Imran et al. ............... 606/41 |
| 5,700,262 A | 12/1997 | Acosta et al. ............... 606/48 |
| 5,715,817 A | 2/1998 | Stevens-Wright et al. ... 600/373 |
| 5,722,975 A | 3/1998 | Edwards et al. ............... 606/41 |
| 5,725,524 A | 3/1998 | Mulier et al. ............... 606/41 |
| 5,749,869 A | 5/1998 | Lindenmeier et al. ............ 606/34 |
| 5,749,871 A | 5/1998 | Hood et al. ............... 606/50 |
| 5,749,914 A | 5/1998 | Janssen ............... 607/116 |
| 5,755,753 A | 5/1998 | Knowlton ............... 607/98 |
| 5,766,153 A | 6/1998 | Eggers et al. ............... 604/114 |
| 5,769,847 A | 6/1998 | Panescu et al. ............... 606/42 |
| 5,785,705 A | 7/1998 | Baker ............... 606/32 |
| 5,786,578 A | 7/1998 | Christy et al. ............... 219/720 |
| 5,800,429 A | 9/1998 | Edwards ............... 606/41 |
| 5,807,395 A | 9/1998 | Mulier et al. ............... 606/41 |
| 5,810,764 A | 9/1998 | Eggers et al. ............... 604/23 |
| 5,810,802 A | 9/1998 | Panescu et al. ............... 606/31 |
| 5,810,809 A | 9/1998 | Rydell ............... 606/49 |
| 5,836,875 A | 11/1998 | Webster, Jr. ............... 600/374 |
| 5,843,019 A | 12/1998 | Eggers et al. ............... 604/22 |
| 5,860,951 A | 1/1999 | Eggers ............... 604/510 |
| 5,860,974 A | 1/1999 | Abele ............... 606/41 |
| 5,860,975 A | 1/1999 | Goble et al. ............... 606/45 |
| 5,871,469 A | 2/1999 | Eggers et al. ............... 604/114 |
| 5,873,855 A | 2/1999 | Eggers et al. ............... 604/114 |
| 5,873,877 A | 2/1999 | McGaffigan ............... 606/41 |
| 5,885,277 A | 3/1999 | Korth ............... 606/35 |
| 5,888,198 A | 3/1999 | Eggers et al. ............... 604/114 |
| 5,891,095 A | 4/1999 | Eggers et al. ............... 604/114 |
| 5,891,134 A | 4/1999 | Goble et al. ............... 606/27 |
| 5,897,553 A | 4/1999 | Mulier ............... 606/41 |
| 5,902,272 A | 5/1999 | Eggers et al. ............... 604/114 |
| 5,944,715 A | 8/1999 | Goble et al. ............... 606/41 |
| 5,954,716 A | 9/1999 | Sharkey et al. ............... 606/32 |
| 5,964,786 A | 10/1999 | Ochs et al. ............... 607/5 |
| 6,004,319 A | 12/1999 | Goble et al. ............... 606/48 |
| 6,013,076 A | 1/2000 | Goble et al. ............... 606/41 |
| 6,015,406 A | 1/2000 | Goble et al. ............... 606/41 |
| 6,024,733 A | 2/2000 | Eggers et al. ............... 604/500 |
| 6,027,501 A | 2/2000 | Goble et al. ............... 606/41 |
| 6,039,734 A | 3/2000 | Goble et al. ............... 606/41 |
| 6,047,700 A | 4/2000 | Eggers et al. ............... 128/898 |
| 6,056,746 A | 5/2000 | Goble et al. ............... 606/48 |
| 6,063,079 A | 5/2000 | Hovda et al. ............... 606/41 |
| 6,066,134 A | 5/2000 | Eggers et al. ............... 606/32 |
| 6,068,628 A | 5/2000 | Fanton et al. ............... 606/41 |
| 6,074,386 A | 6/2000 | Goble et al. ............... 606/34 |
| 6,090,106 A | 7/2000 | Goble et al. ............... 606/41 |
| 6,090,107 A | 7/2000 | Borgmeier et al. ............ 606/41 |
| 6,093,186 A | 7/2000 | Goble et al. ............... 606/34 |
| 6,102,046 A | 8/2000 | Weinstein et al. ............ 128/898 |
| 6,105,581 A | 8/2000 | Eggers et al. ............... 128/898 |
| 6,109,268 A | 8/2000 | Thapliyal et al. ............ 128/898 |
| 6,117,109 A | 9/2000 | Eggers et al. ............... 604/114 |
| 6,126,682 A | 10/2000 | Sharkey et al. ............... 607/96 |
| 6,142,992 A | 11/2000 | Cheng et al. ............... 606/34 |
| 6,149,620 A | 11/2000 | Baker et al. ............... 604/22 |
| 6,159,194 A | 12/2000 | Eggers et al. ............... 604/500 |
| 6,159,208 A | 12/2000 | Hovda et al. ............... 606/41 |
| 6,162,217 A | 12/2000 | Kannenberg et al. ............ 606/34 |
| 6,168,593 B1 | 1/2001 | Sharkey et al. ............... 606/34 |
| 6,174,309 B1 | 1/2001 | Wrublewski et al. ............ 606/45 |
| 6,179,824 B1 | 1/2001 | Eggers et al. ............... 604/500 |
| 6,179,836 B1 | 1/2001 | Eggers et al. ............... 606/45 |
| 6,183,469 B1 | 2/2001 | Thapliyal et al. ............... 606/41 |
| 6,190,381 B1 | 2/2001 | Olsen et al. ............... 606/32 |
| 6,197,021 B1 | 3/2001 | Panescu et al. ............... 606/31 |
| 6,203,542 B1 | 3/2001 | Ellsberry et al. ............... 606/41 |
| 6,210,402 B1 | 4/2001 | Olsen et al. ............... 606/32 |
| 6,210,405 B1 | 4/2001 | Goble et al. ............... 606/41 |
| 6,224,592 B1 | 5/2001 | Eggers et al. ............... 606/32 |
| 6,228,078 B1 | 5/2001 | Eggers ............... 606/32 |
| 6,228,081 B1 | 5/2001 | Goble ............... 606/34 |
| 6,234,178 B1 | 5/2001 | Goble et al. ............... 606/32 |
| 6,235,020 B1 | 5/2001 | Cheng et al. ............... 606/34 |
| 6,237,604 B1 | 5/2001 | Burnside et al. ............... 128/897 |
| 6,238,391 B1 | 5/2001 | Olsen et al. ............... 606/41 |
| 6,238,393 B1 | 5/2001 | Mulier et al. ............... 606/41 |
| 6,254,600 B1 | 7/2001 | Willink et al. ............... 606/41 |
| 6,261,286 B1 | 7/2001 | Goble et al. ............... 606/34 |
| 6,261,311 B1 | 7/2001 | Sharkey et al. ............... 607/96 |
| 6,264,652 B1 | 7/2001 | Eggers et al. ............... 606/41 |
| 6,270,460 B1 | 8/2001 | McCartan et al. ............... 600/459 |
| 6,277,112 B1 | 8/2001 | Underwood et al. ............ 606/32 |
| 6,280,441 B1 | 8/2001 | Ryan ............... 606/45 |
| 6,283,961 B1 | 9/2001 | Underwood et al. ............ 604/41 |
| 6,293,942 B1 | 9/2001 | Goble et al. ............... 606/38 |
| 6,296,636 B1 | 10/2001 | Cheng et al. ............... 606/32 |
| 6,296,638 B1 | 10/2001 | Davison et al. ............... 606/41 |
| 6,306,134 B1 | 10/2001 | Goble et al. ............... 606/42 |
| 6,308,089 B1 | 10/2001 | von der Rur et al. ......... 600/338 |
| 6,309,387 B1 | 10/2001 | Eggers et al. ............... 606/41 |
| 6,312,408 B1 | 11/2001 | Eggers et al. ............... 604/114 |
| 6,322,549 B1 | 11/2001 | Eggers et al. ............... 604/500 |
| 6,346,104 B2 | 2/2002 | Daly et al. ............... 606/34 |
| 6,346,107 B1 | 2/2002 | Cucin ............... 606/49 |
| 6,355,032 B1 | 3/2002 | Hovda et al. ............... 606/32 |
| 6,363,937 B1 | 4/2002 | Hovda et al. ............... 128/898 |
| 6,364,877 B1 | 4/2002 | Goble et al. ............... 606/34 |
| 6,379,351 B1 | 4/2002 | Thapliyal et al. ............... 606/41 |
| 6,391,025 B1 | 5/2002 | Weinstein et al. ............... 606/41 |
| 6,409,722 B1 | 6/2002 | Hoey et al. ............... 606/34 |
| 6,416,507 B1 | 7/2002 | Eggers et al. ............... 606/32 |
| 6,416,508 B1 | 7/2002 | Eggers et al. ............... 606/32 |
| 6,416,509 B1 | 7/2002 | Goble et al. ............... 606/37 |
| 6,432,103 B1 | 8/2002 | Ellsberry et al. ............... 606/41 |
| 6,440,129 B1 | 8/2002 | Simpson ............... 606/42 |
| 6,468,274 B1 | 10/2002 | Alleyne et al. ............... 606/32 |
| 6,468,275 B1 | 10/2002 | Wampler et al. ............... 606/48 |
| 6,482,201 B1 | 11/2002 | Olsen et al. ............... 606/41 |
| 6,514,250 B1 | 2/2003 | Jahns et al. ............... 606/41 |
| 6,517,498 B1 | 2/2003 | Burbank et al. ............... 600/564 |
| 6,530,922 B2 | 3/2003 | Cosman ............... 606/34 |
| 6,558,382 B2 | 5/2003 | Jahns et al. ............... 606/41 |
| 6,565,560 B1 | 5/2003 | Goble et al. ............... 606/41 |
| 6,578,579 B2 | 6/2003 | Burnside ............... 128/897 |
| 6,589,237 B2 | 7/2003 | Woloszko et al. ............... 606/41 |
| 6,602,248 B1 | 8/2003 | Sharps et al. ............... 606/32 |
| 6,620,156 B1 | 9/2003 | Garito et al. ............... 606/50 |
| 6,632,193 B1 | 10/2003 | Davison et al. ............... 604/22 |
| 6,632,220 B1 | 10/2003 | Eggers et al. ............... 606/41 |
| 6,635,034 B1 | 10/2003 | Cosmescu ............... 604/289 |
| 6,656,177 B2 | 12/2003 | Truckai et al. ............... 606/51 |
| 6,702,810 B2 | 3/2004 | McClurken et al. ............ 606/34 |
| 6,730,080 B2 | 5/2004 | Harano et al. ............... 606/38 |
| 6,746,447 B2 | 6/2004 | Davison et al. ............... 606/41 |
| 6,749,604 B1 | 6/2004 | Eggers et al. ............... 606/41 |
| 6,749,608 B2 | 6/2004 | Garito et al. ............... 606/45 |
| D493,530 S | 7/2004 | Reschke ............... D24/144 |
| 6,770,071 B2 | 8/2004 | Woloszko et al. ............... 606/41 |
| 6,780,178 B2 | 8/2004 | Palanker et al. ............... 600/41 |
| 6,780,180 B1 | 8/2004 | Goble et al. ............... 606/41 |
| 6,802,842 B2 | 10/2004 | Ellman et al. ............... 606/45 |
| 6,837,887 B2 | 1/2005 | Woloszko et al. ............... 606/41 |
| 6,837,888 B2 | 1/2005 | Ciarrocca et al. ............... 606/41 |
| 6,866,671 B2 | 3/2005 | Tierney et al. ............... 606/130 |
| 6,878,149 B2 | 4/2005 | Gatto ............... 606/46 |
| 6,890,307 B2 | 5/2005 | Kokate et al. ............... 600/549 |
| 6,892,086 B2 | 5/2005 | Russell ............... 600/372 |
| 6,911,027 B1 | 6/2005 | Edwards et al. ............... 606/40 |
| 6,920,883 B2 | 7/2005 | Bessette et al. ............... 128/898 |

| Patent No. | Date | Inventor | Class |
|---|---|---|---|
| 6,921,398 B2 | 7/2005 | Carmel et al. | 606/41 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,979,328 B2 | 12/2005 | Baerveldt et al. | 606/6 |
| 6,979,601 B2 | 12/2005 | Marr et al. | 438/132 |
| 6,984,231 B2 | 1/2006 | Goble et al. | 606/37 |
| 6,986,770 B2 | 1/2006 | Hood | 606/41 |
| 6,991,631 B2 | 1/2006 | Woloszko et al. | 606/41 |
| 7,001,382 B2 | 2/2006 | Gallo | 606/41 |
| 7,004,941 B2 | 2/2006 | Tvinnereim et al. | 606/41 |
| 7,010,353 B2 | 3/2006 | Gan et al. | 607/50 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,094,231 B1 | 8/2006 | Ellman et al. | 606/37 |
| 7,104,986 B2 | 9/2006 | Hovda et al. | 606/32 |
| 7,115,139 B2 | 10/2006 | McClurken et al. | 607/96 |
| 7,131,969 B1 | 11/2006 | Hovda et al. | 606/45 |
| 7,169,143 B2 | 1/2007 | Eggers et al. | 606/41 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,241,293 B2 | 7/2007 | Davison | 600/410 |
| 7,247,155 B2 | 7/2007 | Hoey et al. | 606/34 |
| 7,270,658 B2 | 9/2007 | Woloszko et al. | 606/32 |
| 7,270,659 B2 | 9/2007 | Hovda et al. | 606/32 |
| 7,270,661 B2 | 9/2007 | Dahla et al. | 606/41 |
| 7,276,061 B2 | 10/2007 | Schaer et al. | 607/41 |
| 7,276,063 B2 | 10/2007 | Davison et al. | 606/45 |
| 7,278,994 B2 | 10/2007 | Goble | 606/41 |
| 7,282,048 B2 | 10/2007 | Goble et al. | 606/34 |
| 7,297,143 B2 | 11/2007 | Woloszko et al. | 606/41 |
| 7,297,145 B2 | 11/2007 | Ormsby et al. | 606/41 |
| 7,318,823 B2 | 1/2008 | Sharps et al. | 606/32 |
| 7,331,956 B2 | 2/2008 | Hovda et al. | 606/32 |
| 7,335,199 B2 | 2/2008 | Goble et al. | 606/41 |
| RE40,156 E | 3/2008 | Sharps et al. | 606/32 |
| 7,344,532 B2 | 3/2008 | Goble et al. | 606/34 |
| 7,357,798 B2 | 4/2008 | Sharps et al. | 606/32 |
| 7,387,625 B2 | 6/2008 | Hovda et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,442,191 B2 | 10/2008 | Hovda et al. | 606/41 |
| 7,445,618 B2 | 11/2008 | Eggers et al. | 604/48 |
| 7,449,021 B2 | 11/2008 | Underwood et al. | 606/32 |
| 7,462,178 B2 | 12/2008 | Woloszko et al. | 607/105 |
| 7,468,059 B2 | 12/2008 | Eggers et al. | 606/32 |
| 7,491,200 B2 | 2/2009 | Underwood et al. | 606/32 |
| 7,507,236 B2 | 3/2009 | Eggers et al. | 606/41 |
| 7,527,624 B2 | 5/2009 | Dubnack et al. | |
| 7,572,251 B1 | 8/2009 | Davison et al. | 604/500 |
| 7,678,069 B1 | 3/2010 | Baker et al. | 604/22 |
| 7,691,101 B2 | 4/2010 | Davison et al. | 606/41 |
| 7,862,560 B2 | 1/2011 | Marion | 606/34 |
| 2002/0029036 A1 | 3/2002 | Goble et al. | 606/38 |
| 2002/0042612 A1 | 4/2002 | Hood et al. | 606/50 |
| 2002/0095151 A1 | 7/2002 | Dahla et al. | 606/41 |
| 2002/0120259 A1 | 8/2002 | Lettice et al. | 606/32 |
| 2002/0151882 A1 | 10/2002 | Marko et al. | 606/28 |
| 2002/0183739 A1 | 12/2002 | Long | |
| 2003/0013986 A1 | 1/2003 | Saadat | 600/549 |
| 2003/0014045 A1 | 1/2003 | Russell | 606/41 |
| 2003/0014047 A1 | 1/2003 | Woloszko et al. | 606/41 |
| 2003/0028189 A1 | 2/2003 | Woloszko et al. | 604/45 |
| 2003/0088245 A1 | 5/2003 | Woloszko et al. | 606/41 |
| 2003/0130655 A1 | 7/2003 | Woloszko et al. | 606/45 |
| 2003/0158545 A1 | 8/2003 | Hovda et al. | 606/32 |
| 2003/0171743 A1 | 9/2003 | Tasto et al. | 606/32 |
| 2003/0181903 A1 | 9/2003 | Hood et al. | 606/49 |
| 2003/0208194 A1 | 11/2003 | Hovda et al. | 606/41 |
| 2003/0208196 A1 | 11/2003 | Stone | 606/41 |
| 2003/0212395 A1 | 11/2003 | Woloszko et al. | 606/32 |
| 2003/0212396 A1 | 11/2003 | Eggers et al. | 606/41 |
| 2003/0216725 A1 | 11/2003 | Woloszko et al. | 606/41 |
| 2003/0216726 A1 | 11/2003 | Eggers et al. | 604/41 |
| 2003/0216732 A1 | 11/2003 | Truckai et al. | 606/49 |
| 2004/0024399 A1 | 2/2004 | Sharps et al. | 606/32 |
| 2004/0030330 A1 | 2/2004 | Brassell et al. | 606/41 |
| 2004/0049180 A1 | 3/2004 | Sharps et al. | 606/32 |
| 2004/0054366 A1 | 3/2004 | Davison et al. | 606/45 |
| 2004/0116922 A1 | 6/2004 | Hovda et al. | 606/41 |
| 2004/0127893 A1 | 7/2004 | Hovda | 606/41 |
| 2004/0153057 A1 | 8/2004 | Davison | 600/410 |
| 2004/0186469 A1 | 9/2004 | Woloszko et al. | 606/41 |
| 2004/0230190 A1 | 11/2004 | Dahla et al. | 604/41 |
| 2005/0004634 A1 | 1/2005 | Hovda et al. | 606/41 |
| 2005/0010205 A1 | 1/2005 | Hovda et al. | 606/32 |
| 2005/0033278 A1 | 2/2005 | McClurken et al. | 606/34 |
| 2005/0119650 A1 | 6/2005 | Sanders et al. | 424/426 |
| 2005/0131402 A1 | 6/2005 | Ciarrocca et al. | 600/450 |
| 2005/0187543 A1 | 8/2005 | Underwood et al. | 606/41 |
| 2005/0234439 A1 | 10/2005 | Underwood et al. | 606/32 |
| 2005/0245923 A1* | 11/2005 | Christopherson et al. | 606/41 |
| 2005/0251134 A1 | 11/2005 | Woloszko et al. | 606/32 |
| 2005/0261754 A1 | 11/2005 | Woloszko et al. | 606/32 |
| 2005/0273091 A1 | 12/2005 | Booth et al. | 607/99 |
| 2005/0288665 A1 | 12/2005 | Woloszko et al. | 606/41 |
| 2006/0036237 A1 | 2/2006 | Davison et al. | 606/41 |
| 2006/0095026 A1 | 5/2006 | Hovda et al. | 606/32 |
| 2006/0095031 A1 | 5/2006 | Ormsby | 606/34 |
| 2006/0129145 A1 | 6/2006 | Ormsby et al. | 606/41 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2007/0010808 A1 | 1/2007 | Dahla | 606/41 |
| 2007/0010809 A1 | 1/2007 | Hovda et al. | 606/32 |
| 2007/0106288 A1 | 5/2007 | Woloszko et al. | 606/41 |
| 2007/0149966 A1 | 6/2007 | Dahla et al. | 606/41 |
| 2007/0161981 A1 | 7/2007 | Sanders et al. | 606/41 |
| 2007/0179497 A1 | 8/2007 | Eggers et al. | 606/41 |
| 2007/0208334 A1 | 9/2007 | Woloszko et al. | 606/41 |
| 2007/0208335 A1 | 9/2007 | Woloszko et al. | 606/41 |
| 2007/0213700 A1 | 9/2007 | Davison et al. | 606/32 |
| 2007/0282323 A1 | 12/2007 | Woloszko et al. | 606/41 |
| 2008/0004621 A1 | 1/2008 | Dahla et al. | 606/48 |
| 2008/0077128 A1 | 3/2008 | Woloszko et al. | 606/41 |
| 2008/0154255 A1 | 6/2008 | Panos et al. | 606/33 |
| 2008/0167645 A1 | 7/2008 | Woloszko | 606/40 |
| 2008/0243116 A1 | 10/2008 | Anderson | 606/41 |
| 2008/0300590 A1 | 12/2008 | Horne et al. | 606/35 |
| 2009/0209956 A1 | 8/2009 | Marion | 606/34 |
| 2010/0152726 A1 | 6/2010 | Cadouri et al. | 606/41 |
| 2010/0228246 A1 | 9/2010 | Marion | 606/37 |
| 2010/0292689 A1 | 11/2010 | Davison et al. | 606/41 |
| 2010/0318083 A1 | 12/2010 | Davison et al. | 606/41 |
| 2010/0324549 A1 | 12/2010 | Marion | 606/37 |
| 2011/0137308 A1 | 6/2011 | Woloszko et al. | 606/41 |

FOREIGN PATENT DOCUMENTS

| | | |
|---|---|---|
| DE | 3930451 A1 | 3/1991 |
| EP | 423757 | 3/1996 |
| EP | 0703461 A2 | 3/1996 |
| EP | 0740926 A2 | 11/1996 |
| EP | 0 754 437 | 1/1997 |
| EP | 0 694 290 | 11/2000 |
| EP | 1334699 | 8/2003 |
| EP | 1428480 | 6/2004 |
| EP | 1707147 | 10/2006 |
| FR | 2313949 | 1/1977 |
| GB | 467502 | 6/1937 |
| GB | 2160102 | 12/1985 |
| GB | 2299216 | 9/1996 |
| GB | 2 308 979 | 7/1997 |
| GB | 2 308 980 | 7/1997 |
| GB | 2 308 981 | 7/1997 |
| GB | 2 327 350 | 1/1999 |
| GB | 2 327 351 | 1/1999 |
| GB | 2 327 352 | 1/1999 |
| GB | 2333455 | 7/1999 |
| GB | 2406793 | 4/2005 |

| | | |
|---|---|---|
| JP | 57-57802 | 4/1982 |
| JP | 57-117843 | 7/1982 |
| NL | 05/000434 | 12/2006 |
| WO | 90/03152 | 4/1990 |
| WO | 90/07303 | 7/1990 |
| WO | 92/21278 | 12/1992 |
| WO | 93/13816 | 7/1993 |
| WO | 93/20747 | 10/1993 |
| WO | 94/04220 | 3/1994 |
| WO | 94/08654 | 4/1994 |
| WO | 94/10921 | 5/1994 |
| WO | 94/26228 | 11/1994 |
| WO | 95/34259 | 12/1995 |
| WO | 96/00040 | 1/1996 |
| WO | 96/00042 | 1/1996 |
| WO | 96/39086 | 12/1996 |
| WO | 97/00646 | 1/1997 |
| WO | 97/00647 | 1/1997 |
| WO | 97/18768 | 5/1997 |
| WO | 97/24073 | 7/1997 |
| WO | 97/24074 | 7/1997 |
| WO | 97/24993 | 7/1997 |
| WO | 97/24994 | 7/1997 |
| WO | 97/43971 | 11/1997 |
| WO | 97/48345 | 12/1997 |
| WO | 97/48346 | 12/1997 |
| WO | 98/07468 | 2/1998 |
| WO | 98/26724 | 6/1998 |
| WO | 98/27879 | 7/1998 |
| WO | 98/27880 | 7/1998 |
| WO | 99/20213 | 4/1999 |
| WO | 99/51155 | 10/1999 |
| WO | 99/51158 | 10/1999 |
| WO | 99/56648 | 11/1999 |
| WO | 00/00098 | 1/2000 |
| WO | 00/09053 | 2/2000 |
| WO | 01/24720 | 4/2001 |
| WO | 01/87154 | 5/2001 |
| WO | 01/95819 | 12/2001 |
| WO | 02/36028 | 5/2002 |
| WO | 02/102255 | 12/2002 |
| WO | 03/024305 | 3/2003 |
| WO | 03/092477 | 11/2003 |
| WO | 2004/026150 | 4/2004 |
| WO | 2004/071278 | 8/2004 |
| WO | 2005/125287 | 12/2005 |
| WO | 2007/006000 | 1/2007 |
| WO | 2007/056729 | 5/2007 |

OTHER PUBLICATIONS

Extended European Search Report for EP09152846, 8pgs, Jan. 5, 2010.
European Search Report for EP 09152850, 2 pgs, Dec. 29, 2009.
European Examination Report for EP 02773432 4 pgs, Sep. 22, 2009.
European Examination Report for EP 04708664 7pgs, Sep. 7, 2009.
European Examination Report for EP 02749601.7 4pgs, Dec. 2, 2009.
UK Search Report for GB0900604.0 4 pgs, May 15, 2009.
Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual" , 15 pgs, Jul. 1991.
Cook et al., "Therapeutic Medical Devices: Application and Design", Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, pp. 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atherosclerotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.

Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of *S. mutans* Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker, R. et al., Abstract P14-11, p. 248, "A Bipolar Electrosurgical Turp Loop", Nov. 1989.
Valley Forge Scientific Corp., "Summary of Safety and Effective Information from 510K", 2pgs, 1991.
Valley Forge's New Products, CLINICA, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202.
PCT International Search Report for PCT/US99/14685, 1 pg, Mailed Oct. 21, 1999.
PCT Notification of International Preliminary Examination Report for PCT/US99/14685, 4 pgs, Mailed Feb. 20, 2001.
PCT International Search Report for PCT/US98/22323, 1 pg, Mailed Mar. 3, 1999.
PCT Notification of International Preliminary Examination Report for PCT/US98/22323, 5 pgs, Mailed Nov. 28, 2000.
European Search Report for EP 98953859, 2 pgs, Jul. 2, 2001.
Supplementary European Search Report for EP 98953859, 3 pgs, Oct. 18, 2001.
PCT International Search Report for PCT/US99/18289, 1 pg, Mailed Dec. 7, 1999.
PCT Notification of International Preliminary Examination Report for PCT/US99/18289, 4 pgs, Mailed Jul. 7, 2000.
European Search Report for EP 99945039.8, 3 pgs, Oct. 1, 2001.
PCT International Search Report for PCT/US02/19261, 1 pg, Mailed Sep. 18, 2002.
PCT International Preliminary Examination Report for PCT/US02/19261, 3 pgs, Mar. 25, 2003.
PCT International Search Report for PCT/US02/29476, 1 pg, Mailed May 24, 2004.
PCT International Search Report for PCT/US03/13686, 1 pg Mailed Nov. 25, 2003.
PCT International Search Report for PCT/US04/03614, 1 pg, Mailed Sep. 14, 2004.
PCT Written Opinion of the International Searching Authority for PCT/US04/03614, 4 pgs, Mailed Sep. 14, 2004.
EP Communication, European Examination Report for EP 98953859.0, 3 pgs, Jun. 14, 2004.
EP Communication, European Examination Report for EP 99945039.8, 5 pgs, May 10, 2004.
PCT Notification of International Search Report and Written Opinion for PCT/US06/26321, 8pgs, Mailed Apr. 25, 2007.
Buchelt, et al. "Excimer Laser Ablation of Fibrocartilage: An In Vitro and In Vivo Study", Lasers in Surgery and Medicine, vol. 11, pp. 271-279, 1991.
Costello et al., "Nd: YAG Laser Ablation of the Prostate as a Treatment for Benign Prostatic Hypertrophy", Lasers in Surgery and Medicine, vol. 12, pp. 121-124, 1992.
Rand et al., "Effect of Elecctrocautery on Fresh Human Articular Cartilage", J. Arthro. Surg., vol. 1, pp. 242-246, 1985.
O'Neill et al., "Percutaneous Plasma Discectomy Stimulates Repair in Injured Porcine Intervertebral Discs", Dept. of Orthopaedic Surgery, Dept. of Radiology Univ. of Cal at San Francisco, CA, 3 pgs.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
BiLAP IFU 910026-001 Rev A for BiLAP Model 3525, J-Hook, 4 pgs, May 20, 1991.
BiLAP Generator Settings, Jun. 1991.
Tucker et al. "The interaction between electrosurgical generators, endroscopic electrodes, and tissue," Gastrointestinal Endoscopy, vol. 38, No. 2, pp. 118-122, 1992.
PCT Notification of the International Search Report and Written Opinion for PCT/US06/60618, 7pgs, Mailed Oct. 5, 2007.
PCT Notification of the International Search Report and Written Opinion for PCT/US07/69856, 7pgs, Mailed Jun. 5, 2008.
Uk Search Report for GB0805062.7 1 pg, Jul. 16, 2008.
European Search Report for EP 02773432 3pgs, Dec. 19, 2008.
European Examination Report for EP 05024974 4 pgs, Dec. 5, 2008.
UK Search Report for GB0800129.9 2pgs, May 8, 2008.
European Search Report for EP 04708664.0 5pgs, Apr. 6, 2009.
PCT Notification of the International Search Report and Written Opinion for PCT/US2011/033784 11 pgs, Mailed Jul. 18, 2011.
PCT Notification of the International Search Report and Written Opinion for PCT/US2011/033761 11 pgs, Mailed Jul. 22, 2011.

* cited by examiner

HARD TISSUE ABLATION SYSTEM

CROSS-REFERENCE TO RELATED APPLICATIONS

This application claims the benefit of Provisional Patent Application No. 60/809,581 filed May 30, 2006, the complete disclosure of which is incorporated herein by reference for all purposes.

FIELD OF INVENTION

This invention relates to an electrosurgical system and method for treating soft and hard body structures; and in particular, a radio-frequency electrosurgical system adapted for treating soft tissues such as ligaments and tendons, and hard tissues such as bone and other mineralized and calcified structures in the body.

BACKGROUND

A convenient and safe system to remove hard tissue such as bone is a long standing challenge. Although a number of approaches exist to remove bone structures including mechanical and electrosurgical devices, the approaches have various shortcomings.

Mechanical devices such as rotary shavers have been used to clean, debride and remove bone. Rotary shavers, however, can lead to excessive bleeding. In order to control bleeding in certain orthopedic procedures, a cauterizing instrument must be utilized to control bleeding of the various tissues.

Electrosurgical devices such as a RF tissue-cutting instruments have been used on various hard tissue structures and deposits. However, RF electrosurgical devices have been found to be generally ineffective at removing bone under suitable surgical conditions.

A safe, effective, and convenient system for removing hard tissue is therefore desirable.

SUMMARY OF THE INVENTION

In one embodiment of the present invention, an electrosurgical system comprises: a shaft, a distal end section, and a(n) active electrode(s) associated with the distal end section; a first fluid supply adapted to deliver a first electrically conductive fluid in the vicinity of the target tissue; and a second fluid supply adapted to deliver a second electrically conductive fluid to the active electrode.

In another embodiment of the present invention, a method comprises: inserting an active electrode in the vicinity of the target tissue in the presence of a first electrically conductive fluid, the first electrically conductive fluid provided from outside of the body; supplying a second electrically conductive fluid in the vicinity of the active electrode; and applying electrical energy to the active electrode to treat the target tissue.

In another embodiment of the present invention, a method comprises: delivering to the target tissue a first electrically conductive fluid supplied from outside of the body; forming plasma from a second electrically conductive fluid; and treating the tissue with the plasma.

In another embodiment of the present invention, a method comprises: identifying a first tissue in a patient; delivering a first electrically conductive fluid from outside the body to the tissue; directing a second electrically conductive fluid to an active electrode in the vicinity of the tissue; applying a radio-frequency voltage to the active electrode in the presence of the second electrically conductive fluid to generate plasma; and modifying the tissue with the plasma.

In an embodiment of the present invention, two external electrically conductive fluid sources are provided. When a radio-frequency voltage is applied between the active electrode and a return electrode in the presence of the fluid, plasma is generated. Depending on a number of factors including the type of electrically conductive fluid being supplied, a soft tissue type may be optimally treated, e.g. ablated. Then, for example, by changing the supply of the electrically conductive fluid, a hard tissue such as a cortical layer of a bone may be ablated. Accordingly, with the present system, procedures that involve treating both soft and hard tissues can be accomplished with one system without the need to switch from one device to another.

Details of embodiments of the present system, methods and apparatus are illustrated in the appended Figures, and described in the following specification.

DETAILED DESCRIPTION

Figure 1:
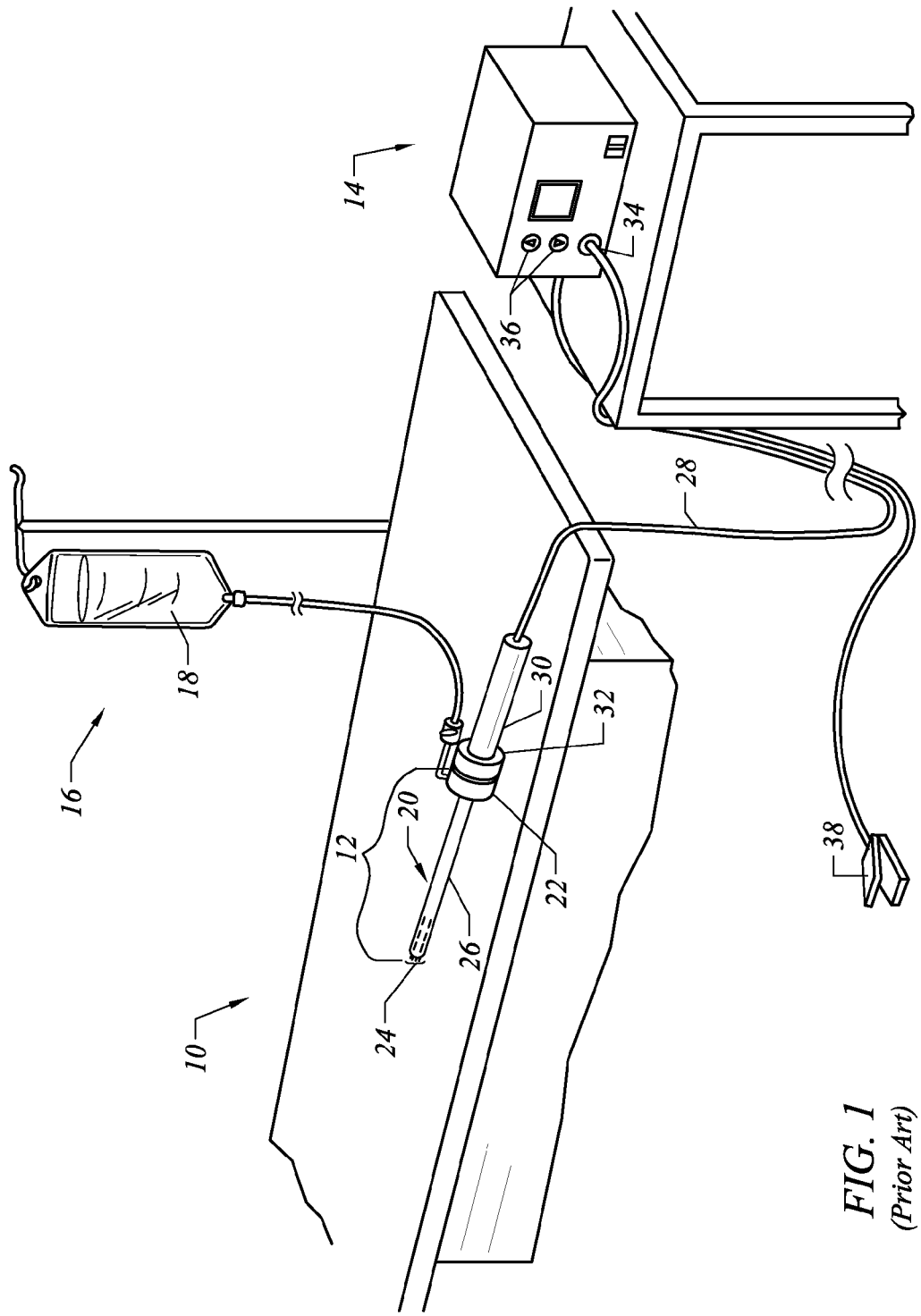
FIG. 1 is an illustration of an electrosurgical system with an electrically conducting fluid source.

An electrosurgical system (10) having only one electrically conductive fluid supply is shown in FIG. 1. It generally comprises an electrosurgical probe (12) connected to a power supply (14) for applying a radio-frequency voltage across an active electrode (24) and a return electrode (not shown) in close proximity of a target tissue, and an electrically conductive liquid source (16) for supplying an electrically conducting fluid (18) to the probe (12) and the target site. Electrosurgical probe (12) includes an elongated shaft (20) that may be flexible, bendable or rigid, with flexible shafts optionally including support cannulas or other structures for accessing the target site.

Figure 2:
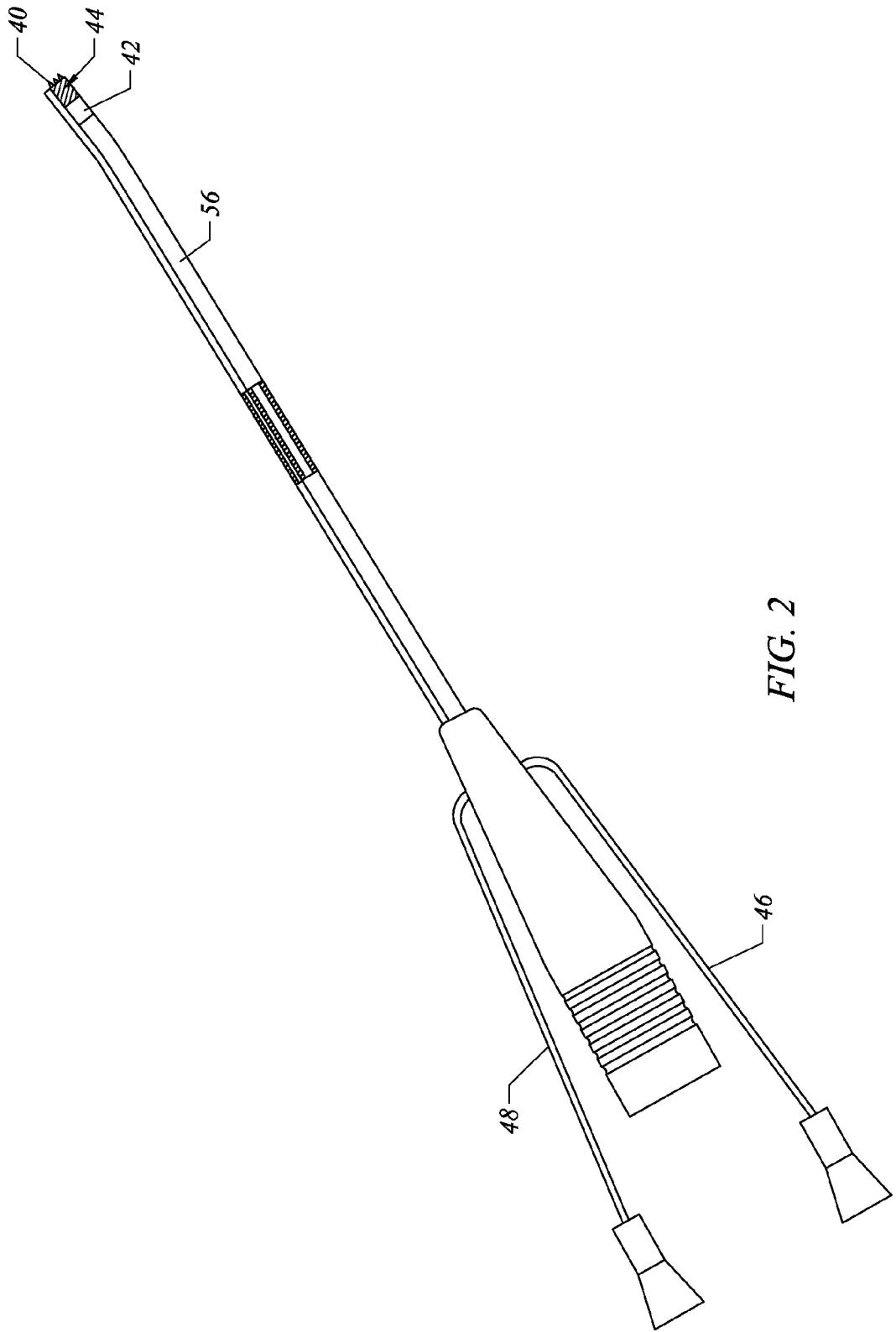
FIG. 2 is an illustration of an electrosurgical probe adaptable for use with the present invention.

In the system illustrated in FIG. 1, the probe (12) includes a probe connector (22) at its proximal end and an array (24) of active electrode terminals disposed on the distal tip of shaft (20). A connecting cable (28) comprising a handle (30) with a handle connector (32) can be removably connected to probe connector (22). Alternatively, a cable may be integrated with the probe (12), and connected to the power supply (14). The proximal portion of electrical cable (28) comprises an electrical connector (34) to couple probe (12) to power supply (14). Referring to FIG. 2, an active electrode (40) and a return electrode (42) are electrically isolated from each other by an insulator (44), and each electrode is connected to an active or passive control circuit within the power supply (14) by a plurality of individually insulated conductors (not shown). A more detailed description of a system is illustrated in U.S. Pat. No. 6,142,992, which is incorporated herein by reference in its entirety. All patents and patent applications that are mentioned herein are incorporated herein by reference in their entirety.

With reference to FIG. 1, power supply (14) comprises a voltage selection switch (36) to change the applied voltage level. Power supply (14) includes a mode selection switch (38) for selectively applying power to the electrode array (24). The foot selection switch (38) may include a second pedal (not shown) for adjusting the voltage level applied to electrode array (24). Specific designs of a power supply are described in commonly assigned U.S. Pat. No. 6,142,992, the entire disclosure of which is incorporated herein by reference.

With reference to FIG. 2, treatment of body tissues typically comprises placing the active electrode (40) in close proximity to, or in contact with the tissue, and applying the voltage across the electrodes (40, 42) to cause changes in the tissue such as heating, ablation, coagulation, cutting, removal, puncturing, and other modifications of the tissue. In particular, plasma may be generated in the vicinity of the active electrode (40) on application of the voltage to the electrodes (40, 42) in the presence of the electrically conductive fluid (18). The plasma includes energetic electrons, ions, photons and the like that are discharged from a vapor layer of the conductive fluid, as described in greater detail in commonly assigned U.S. Pat. No. 5,697,882.

In the system illustrated in FIGS. 1 and 2, the electrically conductive fluid (18) is supplied to the electrodes (40, 42) via a fluid supply lumen (46) coupled to the electrically conductive fluid supply (16). In alternative embodiments, the system optionally includes a fluid aspiration lumen (48) for removing fluids from the target site. In various embodiments, the fluid-supply lumen and the fluid-aspiration lumen are connected to the elongated shaft (20) by flexible fluid lines.

With reference to FIGS. 1 and 2, the electrodes (40, 42) are located on the distal end portion of an electrosurgical shaft (20). In this configuration as is illustrated in FIG. 1, the active electrode (40) is positioned on the shaft at or near the distal end, and the return electrode (42) is positioned close to, but is electrically isolated from the active electrode (40) by an insulator (44).

Figure 3:
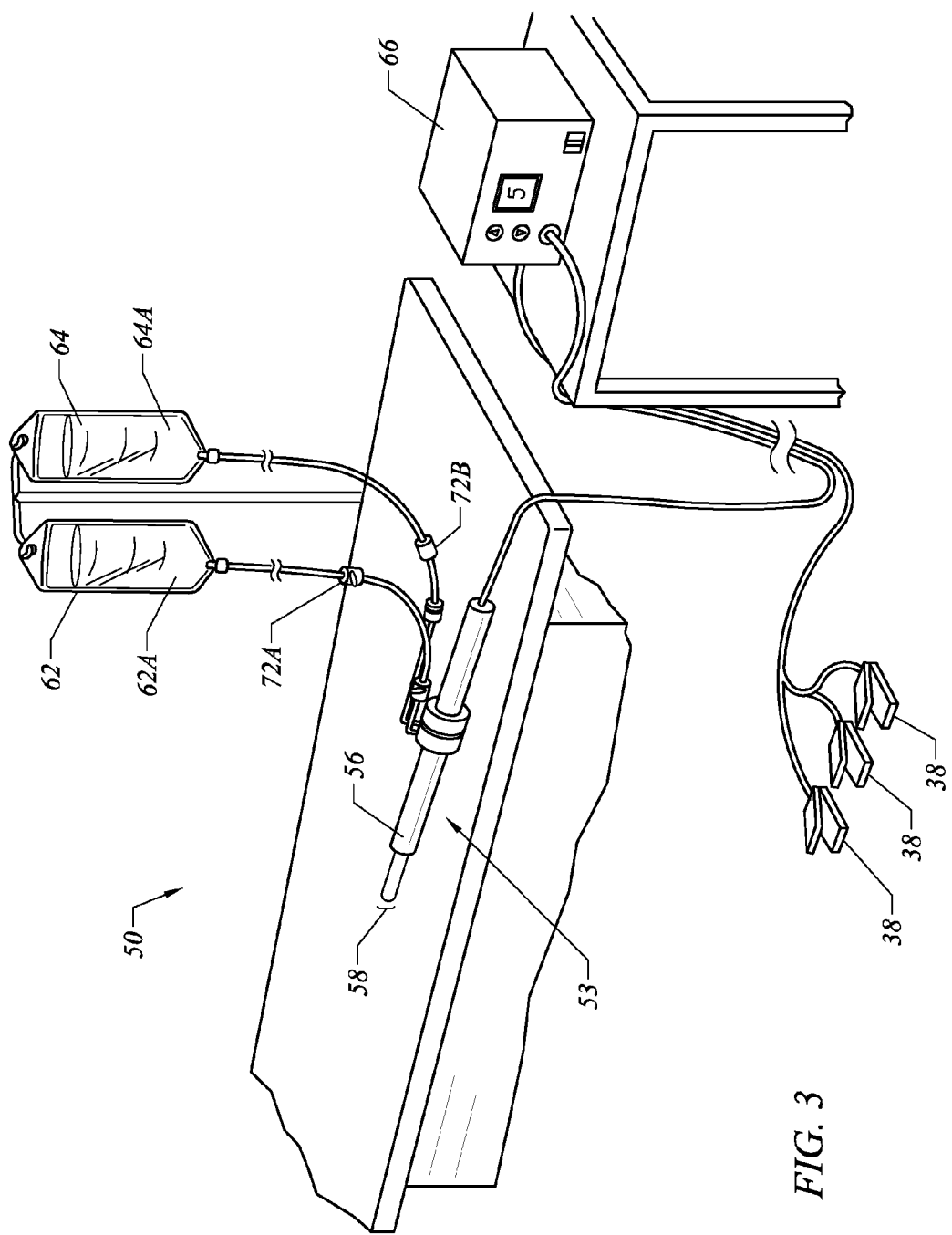
FIG. 3 is an illustration of an embodiment of an electrosurgical system comprising a plurality of electrically conducting fluid supplies.
Figure 4:
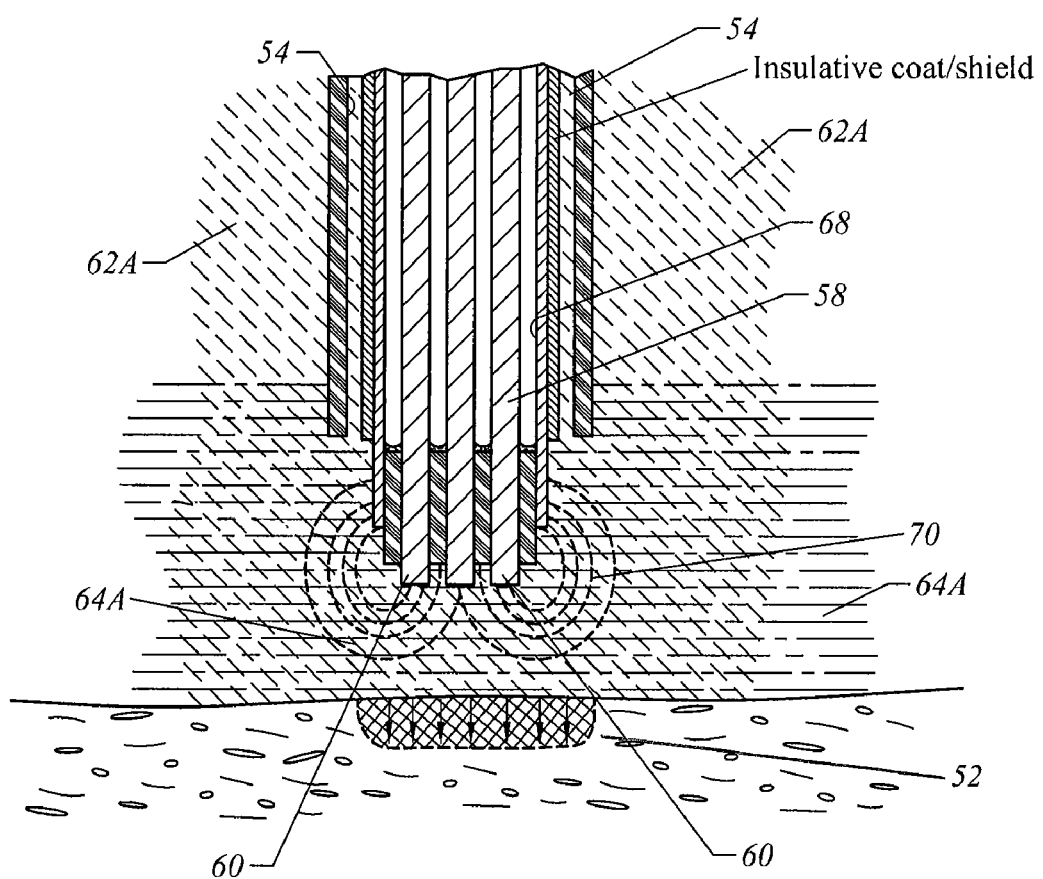
FIG. 4 is an illustration of a distal end of an electrosurgical apparatus immersed in first and second externally supplied electrically conductive fluids.

An embodiment of the present invention is illustrated in FIGS. 3 and 4. System (50) is shown comprising a probe (53) comprising a shaft (56), a distal end section (58), and at least one active electrode (60) associated with the distal end section (58); a first fluid supply (62) adapted to deliver a first electrically conductive fluid (62A) to the target site (52); and a second fluid supply (64) adapted to deliver a second electrically conductive fluid (64A) to the active electrode (60).

In one embodiment the first electrically conductive fluid (62A) is selected from the group consisting of isotonic saline, buffered isotonic saline, hypertonic saline, hypotonic saline, and Ringer's lactate solution. In an exemplary embodiment, the second electrically conductive fluid (64A) is selected from the group consisting of sodium bicarbonate, and a mixture of sodium carbonate and sodium chloride. In another exemplary embodiment, the sodium bicarbonate has a concentration in the range from about 0.15 normal to about 1.0 normal sodium bicarbonate solutions. Exemplary ratios of sodium bicarbonate/sodium chloride concentrations range from about 0.15N/0.15N to about 1.0N/0.15N.

The system includes a voltage supply connected to the active electrode (60) and the return electrode (68), and plasma is generated between the active and return electrode in the presence of the electrically conductive fluids. Each of the first and second electrically conductive fluids (62A, 64A) may be delivered through a lumen extending through the probe. In the embodiment shown in FIG. 4, the second electrically conductive liquid is delivered through annular-shaped lumen (54).

In various embodiments the second electrically conductive fluid supply (64) comprising a sodium bicarbonate solution is adapted to establish a current flow path (70) between the active electrodes (60) and the return electrode (68), while the first electrically conductive fluid provides an electrically conductive fluid environment around the target tissue. The first electrically conductive liquid may be delivered through an annular or other type of opening along the shaft (56). Alternatively, as described in connection with FIG. 7a, the first electrically conductive liquid may be provided through a port or cannula independent of (and separate from) the device (53).

In the embodiment illustrated in FIG. 3, the present system includes adjustable valves (72A, 72B) to control the flow of the first (62A) and second (64A) electrically conductive fluids to the target site. The following are non-limiting examples of treatment that may be performed with the probe of the present invention: molecular dissociation, heating, ablating, coagulating, cutting, removing, excising, resecting, disintegrating, and modifications of the target site.

In the embodiment illustrated in FIG. 3, an adjustable voltage generator is available to regulate the voltage and change the mode of operation of the apparatus. Thus at one voltage setting, the apparatus will generate plasma in the presence of the second conductive fluid in contact with the active electrode; while at another voltage setting plasma generation is minimized and the apparatus causes thermal effects on the tissue such as coagulation, contraction, and vessel hemostasis.

As indicated above, a number of types of hard and soft tissues may be treated. The following are non-limiting examples of hard tissues that may be modified and removed using the present invention: bone, calcified tissue, mineralized tissue, calcified deposits, kidney stones, gall stones, tartar deposits, teeth, calculus and plaque, ossified tissues, and the like. The following are non-limiting examples of soft tissues that may be treated with the present invention: ligament, tendon, bursa, fascia, muscle, intervertebral discs, cartilage, and other soft tissues in the body.

With reference to FIG. 4, the present system in one embodiment comprises a probe having a distal end section (58) that can be placed in contact with (or in close proximity) to a target tissue (52). In particular, the active electrode terminals (60) are in contact or in close proximity with tissue (52). The environment that surrounds the working end of probe is filled with a first electrically conductive fluid (62A) that may, by way of example, be isotonic saline or other biocompatible, electrically conductive irrigant solution. The fluid environment that is in contact with the active electrode at the distal end comprises a second electrically conductive fluid (64A) that is chemically different from the first conductive fluid (62A).

The second or ancillary fluid may be, for example, a sodium bicarbonate solution or another fluid that provides a desired tissue effect. The following are fluids that may be suitable as a second or ancillary injected fluid: acids, such as citric acid, phosphorous acid, hydrochloric acid, etc; bases, such as sodium bicarbonate, sodium hydroxide, etc; chelating agents, such as ethylenediaminetetraacetic acid (EDTA), nitrilotriacetic acid, diethylenetriaminepentaacetic acid, etc; gases, such as nitrogen, helium, argon, etc; as well as hypertonic and hypotonic saline either pH buffered or unbuffered. Some of the above mentioned fluids, as well as various combinations of them, have been found to be effective in causing bone ablation.

The volume of fluid to provide a desired effect (e.g., bone ablation) may vary widely. Relatively small amounts (as little as a few $mm^3$/minute) of injected precursor fluid was sometimes effective in ablating bone. Flowrates greater than 1 or 2 $mm^3$/minute may also be suitable. Aggressive chemicals (strong acids, bases, etc) could be injected locally to the distal end of the device, activated by the plasma, interact with the bone to cause ablation, and then be neutralized and diluted to safe levels in a surrounding buffered isotonic saline field so that untargeted tissue was not exposed to the aggressive precursor or plasma activated chemical species. Alternatively, transient and locally aggressive chemical species formed by the plasma from relatively benign fluids may cause a desired effect as well.

In the system shown in FIGS. 3-4, when a voltage is applied between the active electrode terminals (60) and the return electrode (68), an electrical current flows between the active electrode and the return electrode along current flux lines (70). The current flux lines are shown extending through the second electrically conductive fluid in the region above the surface of the tissue to complete the electrical path between the active electrode terminals and the return electrode. As a consequence of the applied voltage across the active and return electrodes in the presence of the second conductive fluid, plasma is generated around the active electrode and is used to treat or remove the tissue (52).

The system may also be configured to heat and coagulate tissue at a different voltage setting, typically lower than the ablating voltage, due to the electrical impedance of the tissue and the proper selection of the applied voltage and current. Heating of the tissue may occur in a region below the surface of the tissue. The present invention may be used to elevate the temperature of the tissue from normal body temperature (e.g. 37° C.) to a temperature in the range 55° C to 85° C, preferably in the range from 60° C to 70° C.

Figure 5:
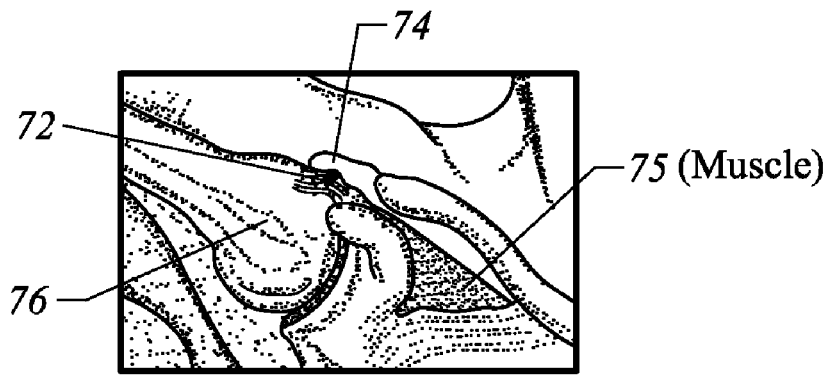
FIG. 5 is an illustration of an inflamed or degenerated supra-spinatus tendon.

FIG. 5 illustrates one condition that may be treated using the system of the present invention. In particular, an inflamed supra-spinatus tendon (72) is shown. The tendon is located between the acromion process (74) and the humerus head (76). This condition may arise for a number of reasons including, for example, excessive use during racquet sports. Friction between the tendon and the bone causes inflammation. Decompressing this region may relieve pain and is therefore desirable.

Figure 6:
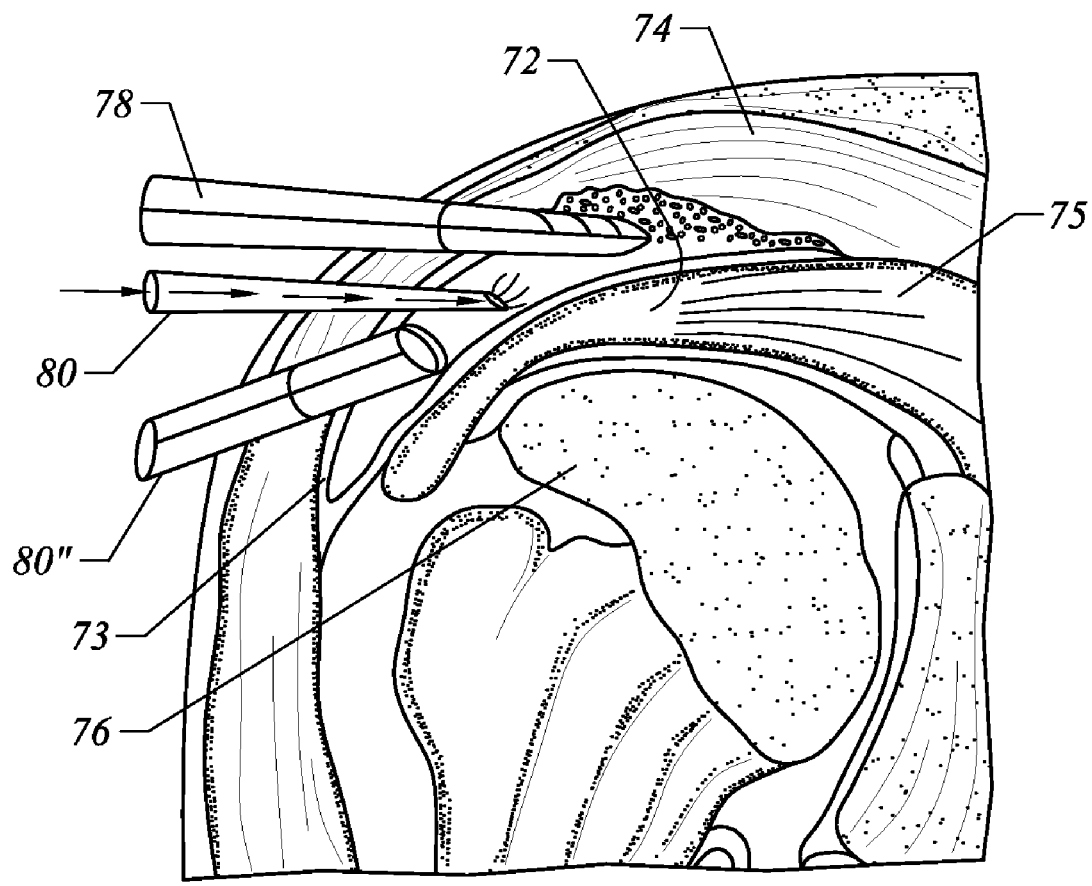
FIG. 6 is an illustration of a rotary shaver treating an inflamed supra-spinatus tendon.

FIG. 6 illustrates decompression whereby tissue and bone is removed to reduce the pressure in the shoulder. Soft tissue including tendon (72), bursa (73) as well as hard bone (74) from the acromion are shown being removed with an electrosurgical shaver or burr (78). As shown in FIG. 6, several tools and instruments are required including: a rotating mechanical instrument such as shaver (78) to remove bone defects, and an electrosurgical tool (not shown) to treat and cauterize the soft tissue; a fluid port (80) to flush and inflate the site; and an arthroscope (80") for visibility. As indicated above, use of a rotary shaver is not always desirable because it may lead to excessive bleeding which may then require a separate coagulating tool.

Figure 7A:
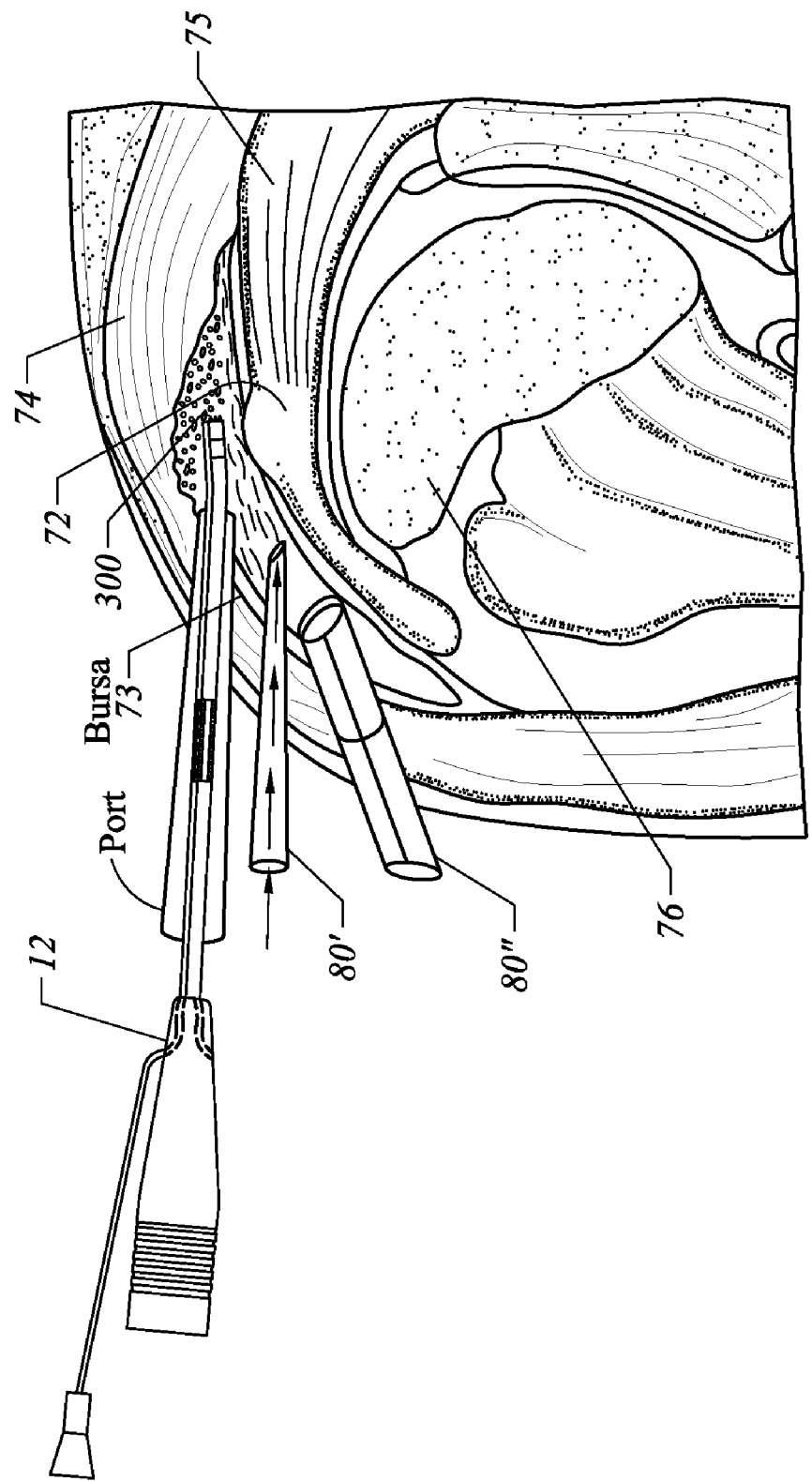
FIG. 7A is an illustration of a device treating an inflamed supra-spinatus tendon.

FIG. 7A illustrates one application of the present invention. In particular, a device 12 is shown being used to perform a subacromonial decompression including the removal of various soft tissue 72. Additionally, the acromion (74) is being ablated. The whole field is filled with a first electrically conductive fluid (which could be buffered isotonic saline, for example). The first fluid is shown being delivered via tube (80'). A second electrically conductive fluid (0.65 N sodium bicarbonate, for example) is injected through device (12) into the vicinity of the active electrode. Without being bound by theory, the second fluid mixes with the first fluid, and is more highly concentrated at its point of injection (300). The plasma that discharges in the highly concentrated second fluid near the active electrode form chemical conditions that are particularly effective at ablating bone at the target site. It is thought that as this second fluid dissipates in the surrounding first fluid the plasma decays and the solution becomes pH neutralized and diluted to levels that are not harmful to surrounding untargeted tissue. In this manner, the acromion is ablated to further relieve pressure or decompress this area.

Additionally, the device (12) has the capability to debride or ablate soft tissues prior to, or after performing the acromioplasty. One way to ablate the soft tissue using device (12) is to shut off the flow of the second liquid. The plasma shall therefore form around the active electrode by vaporizing the first electrically liquid which may, for example, be only effective against one type of tissue such as a tendon, or another tissue.

Depending on the voltage difference applied between the active and the return electrode as indicated above, at any point in time, the device 12 may provide coagulation to halt or arrest bleeding of tissues. In this embodiment, the system of the present invention can decompress the shoulder including sculpting soft tissue, sculpting bone, and coagulating or arresting bleeding.

Figure 7B:
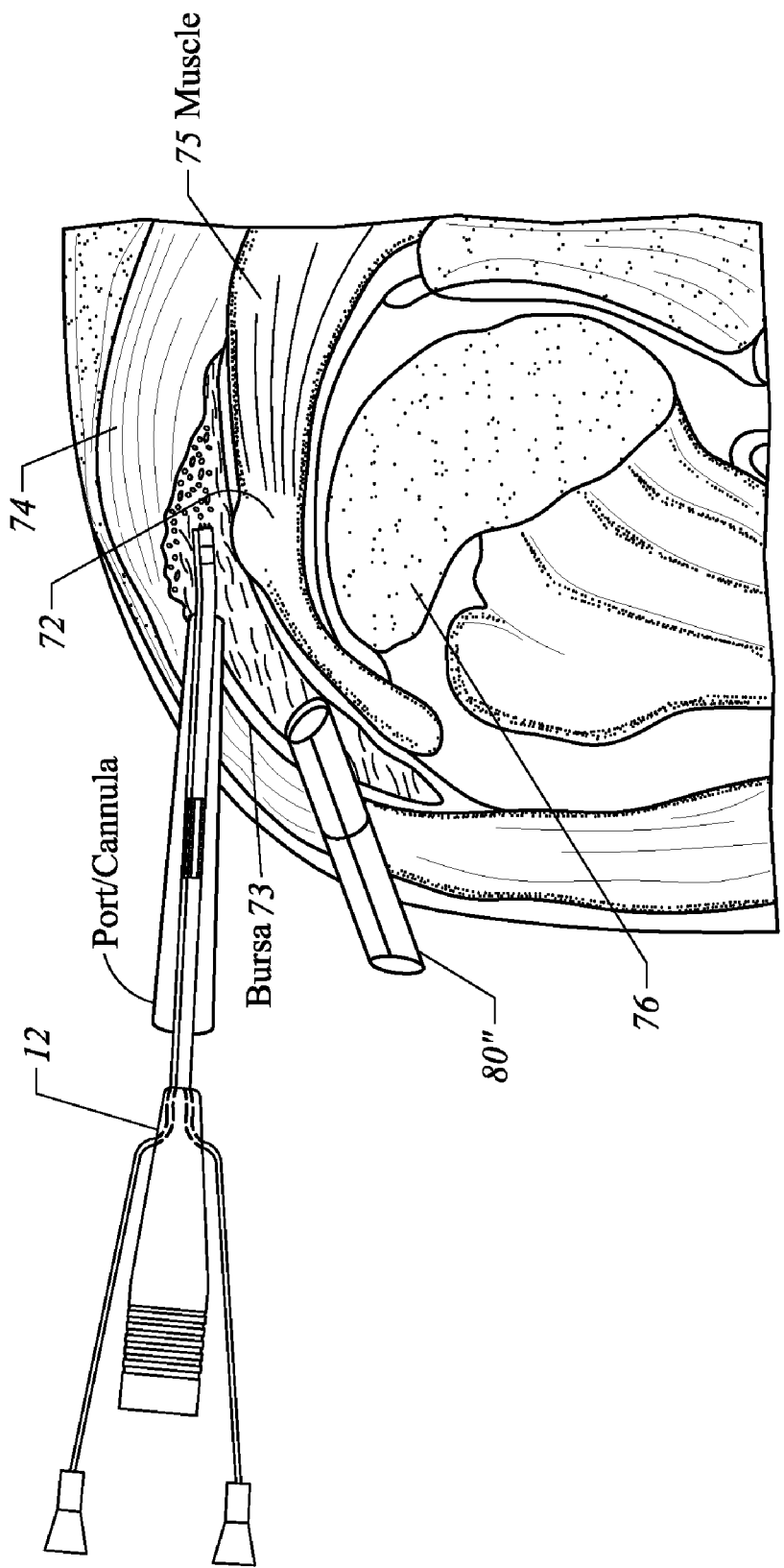
FIG. 7B is an illustration of another device treating an inflamed supra-spinatus tendon.

FIG. 7B illustrates another embodiment of the present invention. In particular, device (12) includes two lumens extending through the shaft of the device corresponding to a first and second electrically conductive liquid supplies. However, it is to be understood that additional lumen may be provided for additional fluid delivery or aspiration. The target site is shown flooded, immersed, or irrigated with the first electrically conductive liquid such as isotonic saline using the first lumen. A second electrically conductive liquid, different than the first liquid, is also injected into the target site through the second lumen. The second electrically conductive liquid is injected preferable near the active electrode such that it is highly concentrated at the point of injection as described above in connection with FIG. 7A. The plasma formed from the second liquid provides enough energy to ablate or molecularly disassociate hard tissue and bone (74). At any point, the flow of the second electrically conductive fluid may be halted, and the device may be activated to treat the soft tissue using the first or another electrically conductive liquid.

Figure 8:
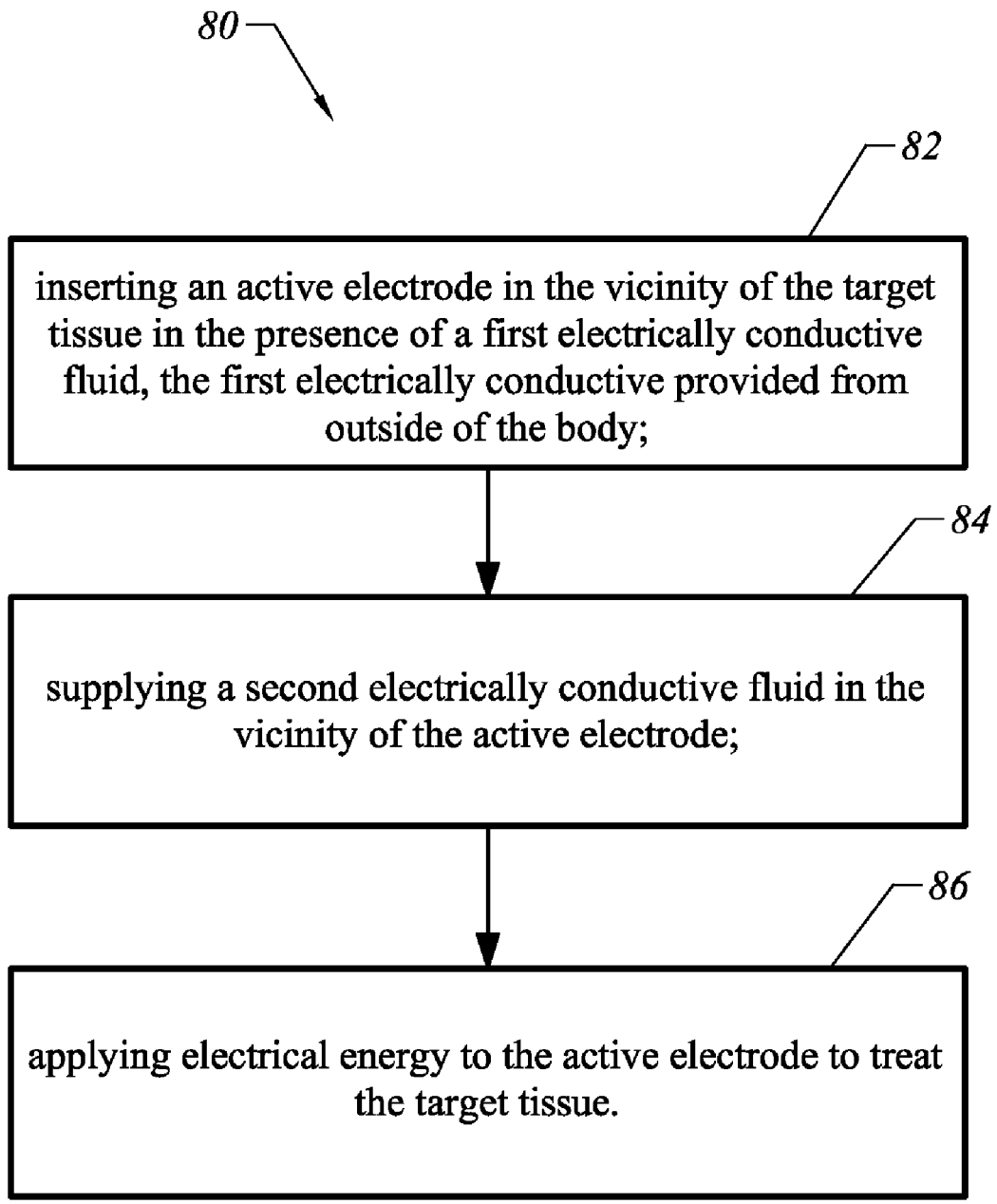
FIG. 8 is an algorithm of a procedure for treating body tissue in accordance with the present invention.

FIG. 8 illustrates a method in accordance with the present invention comprising the steps of: (82) inserting an active electrode in the vicinity of the target tissue (72, 74) in the presence of a first electrically conductive fluid, the first electrically conductive fluid provided from outside of the body; (84) supplying a second electrically conductive fluid in the vicinity of the active electrode; and (86) applying electrical energy to the active electrode to treat the target tissue (72, 74).

Figure 9:
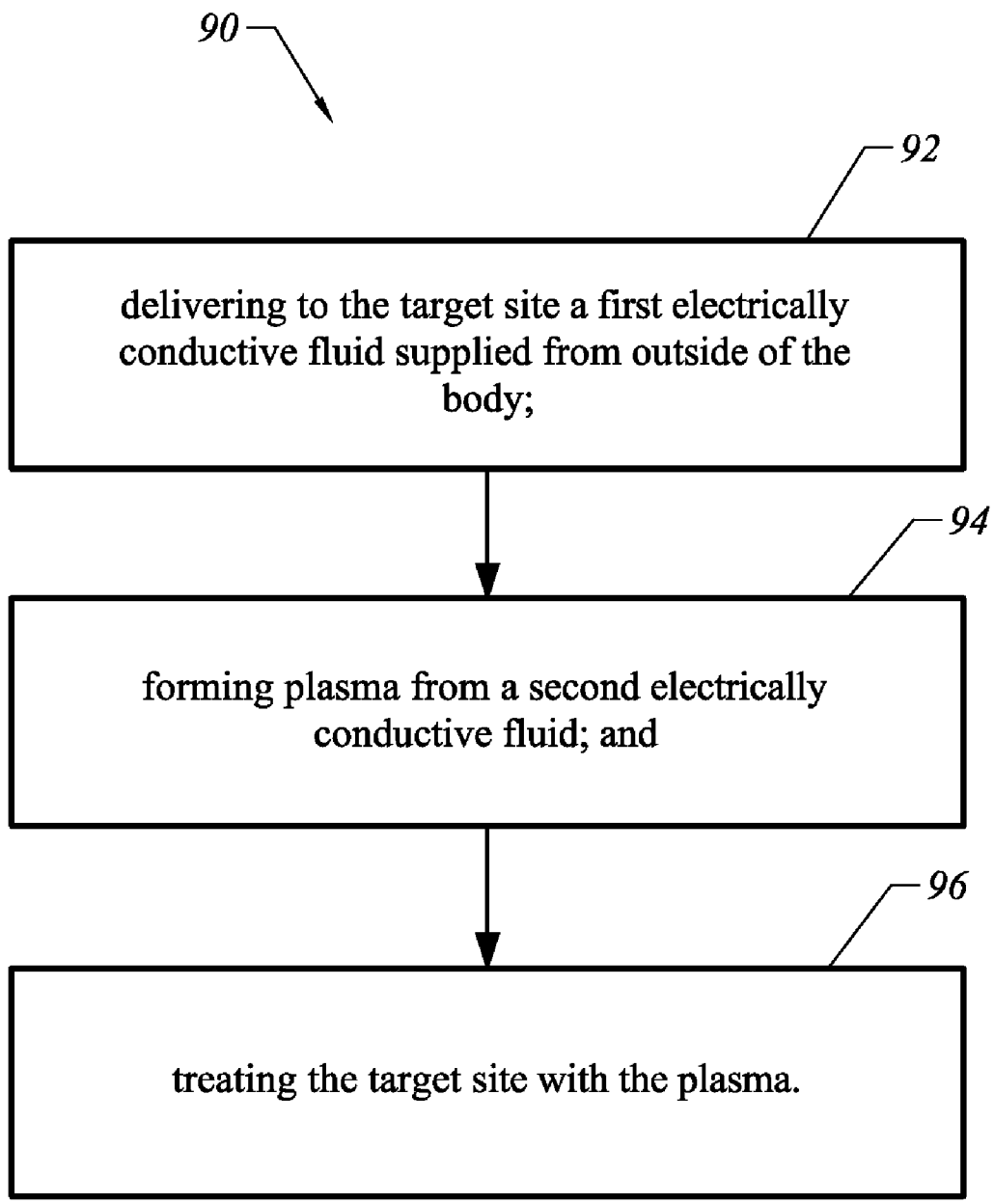
FIG. 9 is an algorithm of a procedure for treating body tissue in accordance with the present invention.

In an alternative embodiment, the tissue (72, 74) is treated by the method (90) set forth in FIG. 9, comprising the steps of:

(92) contacting the target tissue (72, 74) with a first electrically conductive fluid (62A) supplied from outside of the body; forming plasma from a second electrically conductive fluid (64A) around an active electrode (60) in close proximity of the tissue; and treating the tissue with the plasma.

Figure 10:
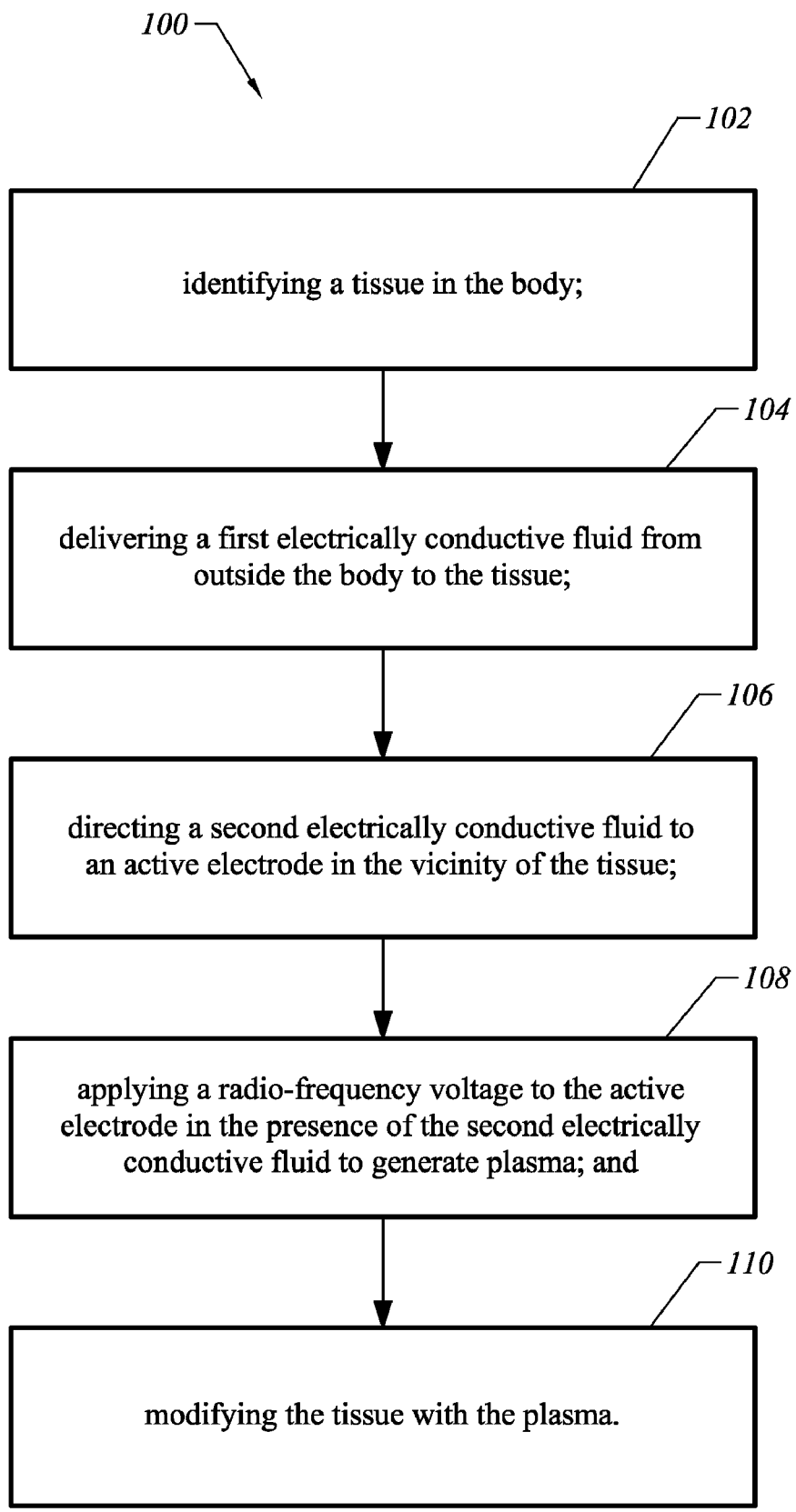
FIG. 10 is an algorithm of a procedure for treating body tissue in accordance with the present invention.

In a further embodiment illustrated in FIG. 10, the tissue (72, 74) is treated by a method (100) comprising the steps of: (102) identifying the tissue in the body; (104) flooding the tissue with a first electrically conductive fluid from outside the body; (106) directing a second electrically conductive fluid to an active electrode in the vicinity of the tissue; (108) applying a radio-frequency voltage to the active electrode in the presence of the second electrically conductive fluid to generate plasma in the vicinity of the active electrode; and (110) using the plasma to modify the first tissue.

The present system and methods are adaptable to treat tissues having various hardness. For example, in treating an articular joint or the acromial bone the soft tissue is first treated by applying a first voltage difference between the active and return electrode in the presence of the electrically conductive fluid. Then, without changing the probe, and using for example a sodium bicarbonate solution, a hard, bony tissue or structure may be modified, ablated or otherwise treated. In an alternative procedure, the hard tissue may be treated prior to treating the soft tissue. In another embodiment of the present invention, both hard and soft structures are treated contemporaneously. Additionally, hemostasis or coagulation may be effected by varying the voltage difference applied between the electrodes.

In another embodiment of the present invention, a visual indicator is included in each conductive fluid to allow a surgeon to quickly distinguish one plasma type from another. An agent may be added to each of the conductive liquids that produces a unique color of plasma. For example, potassium chloride tends to produce a purple colored plasma when added to the first electrically conductive liquid and another chemical (e.g., copper II chloride for bright green, or manganese II chloride for yellow-green) may be added to the second electrically conductive liquid. Thus, the surgeon may observe which mode (or plasma type) is active during a procedure by observing the color of the plasma at the tip of the probe. This safeguards against applying an improper type of plasma (or voltage scheme) on a particular tissue. Indeed, use of one type of plasma may be too aggressive for one type of tissue. Also, use of one type of plasma may be highly ineffective against certain types of tissues or structures.

A manually or electrically controlled valve may be incorporated into the probe, or tubing line to provide various flow rates and mixtures of fluids. While simple fluid injection pressures may be effected using gravity, more advanced pumps may be provided to carefully control the flow rate. Also, the flowrate and injection manifold design may be adjusted to provide a jet-like effect. In one embodiment, fluid flow rates of the second or ancillary fluid may be in the range of about 5 ml/minute to about 65 ml/minute.

EXAMPLE

Figure 11A:
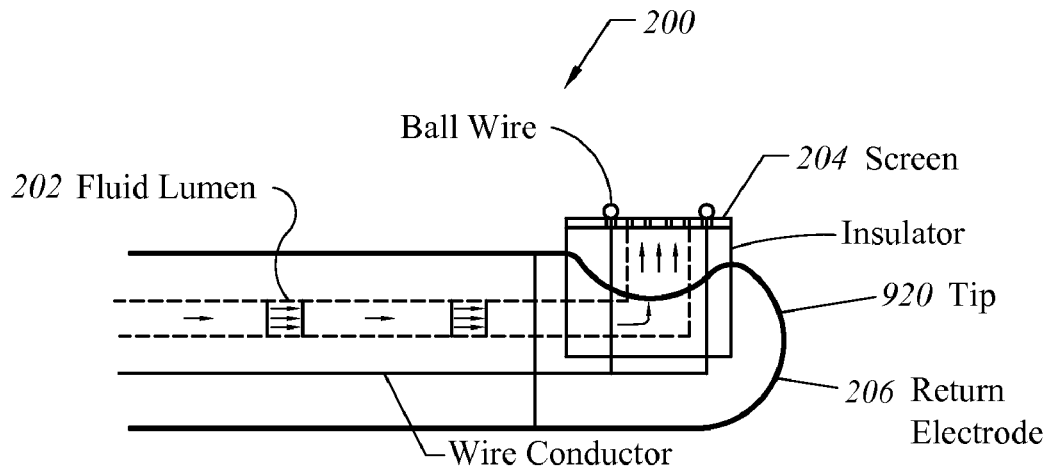
FIG. 11A is a cross sectional view of a distal end of an electrosurgical device having an active electrode member and adapted to deliver an electrically conductive fluid in the vicinity of the active electrode.
Figure 11B:
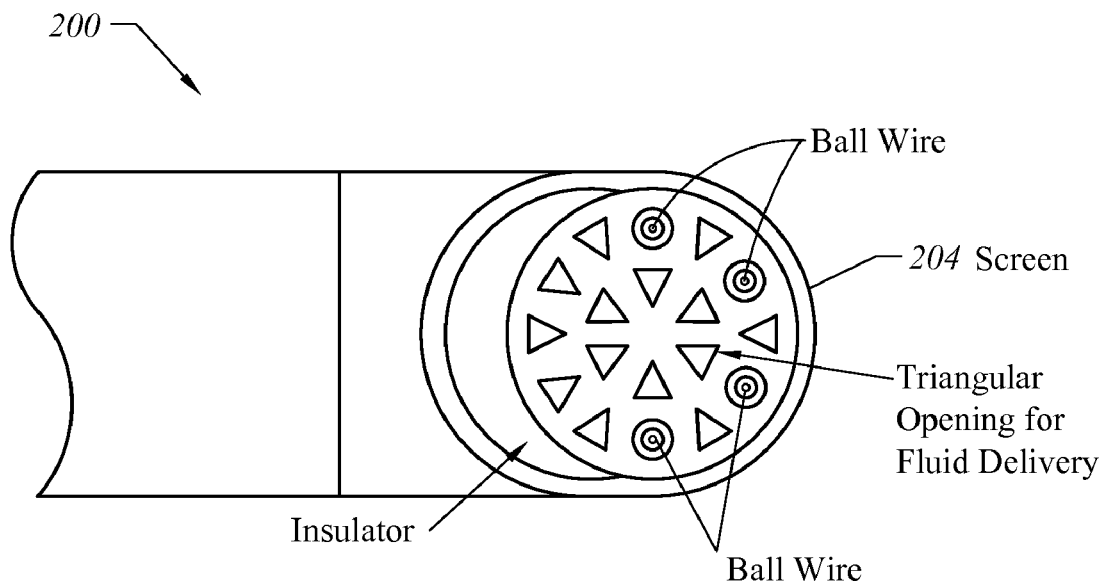
FIG. 11B is a top view of the device shown in FIG. 11A.

One embodiment of the present invention was used to treat a porcine rib cortical bone. The bone was immersed in a first static electrically conductive fluid. A second ancillary liquid comprising a 0.5 N sodium bicarbonate and 0.9% (w/w) sodium chloride (unbuffered) was disposed around an active electrode. The device was similar to the probe (200) shown in FIG. 11A,B. The ancillary liquid was injected around the active electrode at flow rate of about 5 milliliters per minute through lumen (202). The first static solution comprised buffered isotonic saline (0.9% w/w NaCl in water, buffered to pH=7.0-7.2). A voltage of approximately 390 volts rms (root mean square), 551 volts amplitude was applied across the active electrode (204) and the return electrode (206), while the electrode (204) was moved over the bone with light tactile force. After 1 minute of treatment the voltage was turned off and the sample examined. A bone removal rate of approximately 72.8 cubic millimeters per minute was determined from the dimensions of the zone of removed bone and the treatment time.

A wide variety of surgical applications may be performed using the probe, system and methods of the present invention including, but not limited to: endovascular surgery, peripheral vascular surgery, coronary vascular surgery, (e.g., atherectomy), spine surgery (e.g., discectomy), orthopedic surgery (e.g., acromioplasty, subacromial decompression), craniofacial surgery, oral surgery (e.g., tonsillectomy), urologic surgery (e.g., calcific stone removal), dental specialties including endodontics, periodiontics, and general dentistry.

By the present description and Figures it is to be understood that the terms used herein are descriptive rather than limiting, and that changes, modifications, and substitutions may be made without departing from the scope of the invention. Therefore the invention is not limited to the embodiments described herein, but is defined by the scope of the appended claims. Additionally, all features and aspects of the above described embodiments and examples may be combined with other aspects and examples set forth above. All such combinations that are not mutually exclusive are also part of the present invention.

What is claimed is:

1. A method of treating a target structure in a body, comprising:
    inserting an active electrode in the vicinity of the target structure in the presence of a first electrically conductive fluid, the first electrically conductive fluid provided from outside of the body;
    selectively supplying a second electrically conductive fluid distinct from the first electrically conductive fluid in the vicinity of the active electrode; and
    applying electrical energy to the active electrode in the presence of the second conductive fluid sufficient to create a plasma that discharges in the second electrically conductive fluid and treat the target structure, while the first electrically conductive fluid provides a neutralizing barrier to sufficiently dilute the second electrically conductive fluid such that exposure of the second electrically conductive fluid to an untargeted tissue is not harmful.

2. The method of claim 1, wherein the step of applying electrical energy causes at least one of: molecular dissociation, heating, ablating, coagulating, cutting, removing, and modifying of the target tissue.

3. The method of claim 1, further comprising the step of stopping the supply of the second fluid before treating a soft tissue selected from the group consisting of a ligament, a tendon, a bursa, a muscle, an intervertebral disc and cartilage.

4. The method of claim 3, further comprising the step of applying electrical energy to the active electrode sufficient to discharge a second plasma in the first conductive fluid to treat the soft tissue.

5. The method of claim 1, wherein treating the target structure comprises treating a hard body structure selected from the group consisting of a bone, a calcified tissue, a mineralized tissue, a calcified deposit, kidney stones, gall stones, tartar deposits, a tooth, and plaque.

6. The method of claim 1, wherein treating the target structure comprises treating a mineralized deposit in the body.

7. The method of claim 1, comprising treating a target tissue selected from the group consisting of an articular joint and an acromion.

8. The method of claim 1, comprising treating a soft tissue subsequent to treating a hard tissue.

9. The method of claim 1, wherein supplying the second electrically conductive fluid comprises supplying sodium bicarbonate solution.

10. The method of claim 1, wherein the plasma discharge from the second electrically conductive fluid is particularly effective at ablating bone tissue.

11. The method of claim 1, wherein the first electrically conductive fluid comprises a first indicator that effects the color of the plasma from said first fluid.

12. The method of claim 11, wherein the first indicator comprises potassium chloride.

13. The method of claim 1, comprising stopping the flow of the second electrically conductive fluid to the active electrode site when treating soft tissue.

14. A method of treating a target structure in a body, comprising:
delivering to the target structure a first electrically conductive fluid supplied from outside of the body;
forming plasma from a second electrically conductive fluid that is chemically distinct from the first electrically conductive fluid while the first electrically conductive fluid provides a neutralizing barrier to sufficiently dilute the second fluid such that exposure of the second electrically conductive fluid to an untargeted tissue is not harmful; and
treating the structure with the plasma.

15. The method of claim 14, wherein the first electrically conductive fluid is selected from the group consisting of: isotonic saline, hypertonic saline, hypotonic saline, and Ringer's lactate solution.

16. The method of claim 14, wherein the second electrically conductive fluid comprises sodium bicarbonate.

17. The method of claim 14, wherein treating the target structure comprises treating a hard body structure selected from the group consisting of a bone, a calcified tissue, a mineralized tissue, a calcified deposit, kidney stones, gall stones, tartar deposits, a tooth, and plaque.

18. A method of modifying a structure in a body, comprising:
identifying a body structure in a patient;
delivering a first electrically conductive fluid from outside the body to the area surrounding and including the body structure;
selecting a second electrically conductive fluid effective in treating said body structure and that is chemically distinct from the first electrically conductive fluid,
directing the second electrically conductive fluid to an active electrode in the vicinity of the body structure; and
applying a radio-frequency voltage to the active electrode in the presence of the second electrically conductive fluid sufficient to create a plasma that discharges in the second electrically conductive fluid and such that the body structure is modified while the first electrically conductive fluid provides a neutralizing barrier to sufficiently dilute the second electrically conductive fluid such that exposure of the second electrically conductive fluid to an untargeted tissue is not harmful.

19. The method of claim 18, wherein identifying the structure comprises identifying a hard body structure selected from the group consisting of a bone, a calcified tissue, a mineralized tissue, a calcified deposit, kidney stones, gall stones, tartar deposits, a tooth, and plaque.

20. The method of claim 18, wherein identifying the structure comprises identifying a soft tissue selected from the group consisting of a ligament, a tendon, a muscle, cartilage, and an intervertebral disc.

21. The method of claim 18, wherein delivering first electrically conductive fluid comprises flooding the structure with an electrically conductive fluid selected from the group consisting of: isotonic saline, hypertonic saline, hypotonic saline, and Ringer's lactate solution.

22. The method of claim 18, wherein directing a second electrically conductive fluid comprises directing a solution of sodium bicarbonate to the active electrode.

23. The method of claim 18, wherein the body structure is modified only where the second electrically conductive fluid is sufficiently concentrated while mixed with the first electrically conductive fluid.

* * * * *